United States Patent
Fujii et al.

(10) Patent No.: US 11,655,381 B2
(45) Date of Patent: May 23, 2023

(54) SOLVENT COMPOSITION FOR ELECTRONIC DEVICE PRODUCTION

(71) Applicant: DAICEL CORPORATION, Osaka (JP)

(72) Inventors: Hiroyuki Fujii, Himeji (JP); Yasuyuki Akai, Himeji (JP); Youji Suzuki, Himeji (JP)

(73) Assignee: DAICEL CORPORATION, Osaka (JP)

( * ) Notice: Subject to any disclaimer, the term of this patent is extended or adjusted under 35 U.S.C. 154(b) by 552 days.

(21) Appl. No.: 16/606,550

(22) PCT Filed: Apr. 25, 2018

(86) PCT No.: PCT/JP2018/016761
§ 371 (c)(1),
(2) Date: Oct. 18, 2019

(87) PCT Pub. No.: WO2018/199144
PCT Pub. Date: Nov. 1, 2018

(65) Prior Publication Data
US 2021/0115272 A1   Apr. 22, 2021

(30) Foreign Application Priority Data

Apr. 28, 2017   (JP) ................ JP2017-090195

(51) Int. Cl.
| | |
|---|---|
| *H01M 8/00* | (2016.01) |
| *C09D 11/033* | (2014.01) |
| *C07C 233/58* | (2006.01) |
| *H05K 3/12* | (2006.01) |
| *H05K 1/09* | (2006.01) |

(52) U.S. Cl.
CPC .......... *C09D 11/033* (2013.01); *C07C 233/58* (2013.01); *H05K 3/12* (2013.01); *H05K 3/1291* (2013.01); *H05K 1/092* (2013.01); *H05K 3/1283* (2013.01)

(58) Field of Classification Search
CPC ............ H01M 8/00; H05K 3/00; C23C 14/00
See application file for complete search history.

(56) References Cited

U.S. PATENT DOCUMENTS

| | | | |
|---|---|---|---|
| 2009/0233237 A1* | 9/2009 | Yoshiki .................. | H05K 3/106 430/311 |
| 2010/0022078 A1* | 1/2010 | Rockenberger ... | H01L 29/66143 257/E21.295 |
| 2012/0177897 A1* | 7/2012 | Jablonski .............. | C23C 24/106 977/773 |
| 2014/0221543 A1* | 8/2014 | Wang ...................... | B22F 1/054 524/403 |

FOREIGN PATENT DOCUMENTS

| | | | |
|---|---|---|---|
| CN | 102573313 A | * | 7/2012 |
| CN | 102883543 B | * | 4/2016 |
| JP | H10273477 A | * | 10/1998 |
| JP | 2006-299030 A | | 11/2006 |
| JP | 2009-155592 A | | 7/2009 |
| WO | WO 2016/125618 A1 | | 8/2016 |
| WO | WO 2016/158969 A1 | | 10/2016 |

OTHER PUBLICATIONS

JP H10273477 A, English translated, Hanabusa, (Year: 1998).*
CN 102883543 B, English translated, Chang, (Year: 2016).*
"The estimation of modified nonspecific solubility parameter of liquids by correlation with refractive index and molar energies of vaporization", Tim Uzomah, Global Journal of Pure and Appueo mrnm vol. 7, No. I Jan. 2001:67-72 (Year: 2001 ).*
CN 102573313 A, Google Patents (Year: 2012).*
Doherty et al., "Small Molecule Cyclic Amide and Urea Based Thickeners for Organic and sc-CO$_2$/Organic Solutions," Energy Fuels (2016), vol. 30, pp. 5601-5610.
Extended European Search Report dated Jan. 14, 2021, in European Patent Application No. 18791479.1.
Shikata et al., "Viscoelastic Behavior Of a Supramolecular Polymeric System Consisting of Tri-3,7-dimethyloctyl cis-1 ,3,5-cyclohexanetricarboxaminde and n-Decane," Journal of the Society of Rheology, Japan (2003), vol. 31, No. 4, pp. 229-236.
Hanabusa et al., "Small Molecular Gelling Agents to Harden Organic Liquids: Trialkyl cis-1,3,5-Cyclohexanetricarboxamides," Chemistry Letter (1997), vol. 3, pp. 191-192.

(Continued)

*Primary Examiner* — David P Turocy
*Assistant Examiner* — Mohammad Mayy
(74) *Attorney, Agent, or Firm* — Birch, Stewart, Kolasch & Birch, LLP

(57) ABSTRACT

The present invention provides a solvent composition for use in an ink for producing an electronic device using a printing method, the solvent composition being capable of improving the printing accuracy of the ink, being fired at low temperatures, and suppressing the amount of ash remaining after firing to a very low amount. The solvent composition for electronic device production of the present invention is for use in an ink for producing an electronic device by a printing method, and contains a miscible product of: a solvent and a compound represented by Formula (1) below. In Formula (1), R represents the same or different aliphatic hydrocarbon groups having 1 or more carbon atoms.

[Chem. 1]

(1)

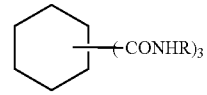

18 Claims, No Drawings

(56) References Cited

OTHER PUBLICATIONS

Hanabusa et al.. "Synthesis of Low Molecular Weight Organogeiators and Their Physical Gelation", Japanese Journal of Polymer Science and Technology (Oct. 1998), vol. 55, No. 10, pp. 585-594 (with English Abstract).
International Search Report dated Jul. 24, 2018, in PCT/JP2018/016761.
Sakamoto et al., "Controlled Large Macrodipoies in a Supramolecular Polymer of Tri-3,7-dimethyloctyl-cis-1,3,5-cyclohexane-tricarboxamide in η-Decane," Macromolecules (2005), vol. 38, pp. 8983-8986.
Written Opinion dated Jul. 24, 2018, in PCT/JP2018/016761.

\* cited by examiner

SOLVENT COMPOSITION FOR ELECTRONIC DEVICE PRODUCTION

TECHNICAL FIELD

The present invention relates to a solvent composition used in inks for producing electronic devices by a printing method. The present application claims priority to JP 2017-090195 filed in Japan on Apr. 28, 2017, the content of which is incorporated herein.

BACKGROUND ART

Electronic devices produced using printing methods include, capacitors, inductors, varistors, thermistors, transistors, speakers, actuators, antennas, and solid oxide fuel cells.

For example, laminated ceramic capacitors are generally produced as described below.
1. Molding a slurry containing a ceramic powder, a binder resin such as a polyvinyl acetal resin, and a solvent into a sheet shape to obtain a green sheet.
2. Applying an ink containing an electrical property imparting material (for example, nickel and palladium), a binder resin (for example, ethyl cellulose), and an organic solvent (for example, terpineol) onto the green sheet by a printing method to form wiring, electrodes, and the like (hereinafter, also referred to as "wiring and the like") of a conductive circuit (application).
3. Drying the applied ink (drying).
4. Cutting to a predetermined dimension the green sheet on which the wiring and the like are formed, and stacking and pressure bonding a plurality of the cut sheets.
5. Firing the stacked and pressure bonded sheets (firing).

The binder resin included in the ink functions to fix the electrical property imparting material on the green sheet, and to impart an appropriate degree of viscosity and enable the formation of a fine printed pattern. Typically, ethyl cellulose has been primarily used as the binder resin. However, the use of ethyl cellulose has resulted in problems. Namely, ethyl cellulose, because of its low thermal decomposability, must be fired at high temperatures, and a member including a coated surface (hereinafter, may be referred to as a "coated surface member") may soften and deform due to exposure to high temperatures for a long period of time, and furthermore, carbon components remain as ash after firing, leading to a reduction in conductivity.

In order to solve the problems described above, various improvements for the binder resin have been investigated. For example, Patent Document 1 discloses that the amount of ash produced can be reduced by using a polyvinyl acetal resin in place of ethyl cellulose. However, even when a polyvinyl acetal resin was used, satisfactory results with respect to these problems were not obtained.

CITATION LIST

Patent Document

Patent Document 1: JP 2006-299030 A

SUMMARY OF INVENTION

Technical Problem

Therefore, an object of the present invention is to provide a solvent composition for use in an ink for electronic device production using a printing method, and a method for producing the same, the solvent composition being capable of: improving the printing accuracy of the ink, being fired at low temperatures, and suppressing the amount of ash remaining after firing to a very low level.

Another object of the present invention is to provide an ink for producing an electronic device by a printing method, which excels in printing accuracy, is capable of being fired at low temperatures, and has a very low amount of ash remaining after firing.

Solution to Problem

As a result of diligent research to solve the problems described above, the present inventors discovered that: when a compound represented by Formula (1) below (hereinafter, also referred to as "compound (1)") is miscible with a solvent, the compound (1) becomes self-assembled in the solvent to form a string-shaped associated body, resulting in a viscosity as that of a polymer compound, and thus an effect of increasing the viscosity of the solvent is demonstrated; the firing can be performed at a lower temperature than that for a binder resin such as ethyl cellulose; and the amount of ash remaining after firing is extremely low.

The present inventors also discovered that: the ink containing the miscible product of the compound (1) and solvent has a viscosity that is suitable for forming wiring and the like, and therefore liquid dripping can be suppressed, and a wiring pattern with high accuracy can be formed by a printing method; in the firing, compared to a case in which an ink containing a binder resin such as ethyl cellulose is fired, firing can be performed quickly at a lower temperature, and softening and deformation of the coated surface member due to exposure to high temperatures for a long period of time can be prevented; and the amount of ash remaining after firing even at low temperatures can be significantly reduced, thereby suppressing a reduction in electrical properties caused by the ash. The present invention was completed based on these findings.

That is, the present invention provides a solvent composition for electronic device production, which is used in an ink for producing an electronic device by a printing method, the solvent composition containing a miscible product of: a solvent and a compound represented by Formula (1) below:

[Chem. 1]

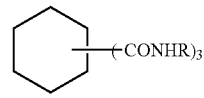

(1)

wherein R is the same or different and represents an aliphatic hydrocarbon group having 1 or more carbon atoms.

The present invention also provides the solvent composition for electronic device production, wherein R in Formula (1) is a linear or branched chain alkyl group, alkenyl group, or alkynyl group having from 6 to 25 carbon atoms.

The present invention also provides the solvent composition for electronic device production, wherein an SP value $[(cal/cm^3)^{0.5}]$ of the solvent at 25° C. is from 7.0 to 9.0.

The present invention also provides the solvent composition for electronic device production, wherein the solvent is at least one selected from n-decane, n-dodecane, propylene glycol methyl-n-propyl ether, propylene glycol methyl-n-butyl ether, dipropylene glycol dimethyl ether, dipropylene glycol methyl-n-propyl ether, dipropylene glycol methyl-n-butyl ether, dipropylene glycol methyl isoamyl ether, tripropylene glycol methyl-n-propyl ether, cyclohexyl acetate, 2-methylcyclohexyl acetate, 4-t-butylcyclohexyl acetate, and dihydroterpinyl acetate.

The present invention also provides the solvent composition for electronic device production, wherein a weight ratio of the solvent to the compound represented by Formula (1) constituting the miscible product (the solvent:the compound) is from 100:0.01 to 100:50.

The present invention also provides a method for producing a solvent composition for electronic device production, wherein the solvent composition for electronic device production is obtained through blending a solvent and a compound to make a miscible material, the compound being represented by the Formula (1) below:

[Chem. 2]

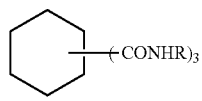

(1)

wherein R is the same or different and represents an aliphatic hydrocarbon group having 1 or more carbon atoms.

The present invention also provides an ink for electronic device production, the ink containing a miscible product of: a solvent and a compound represented by Formula (1) below:

[Chem. 3]

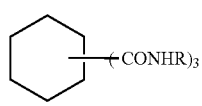

(1)

wherein R is the same or different and represents an aliphatic hydrocarbon group having 1 or more carbon atoms.

The present invention also provides the ink for electronic device production, further containing an electrical property imparting material.

The present invention also provides the ink for electronic device production, wherein a binder resin content is 10 wt. % or less.

Advantageous Effects of Invention

The solvent composition for electronic device production according to the present invention has an appropriate viscosity.

In addition, the ink containing the solvent composition for electronic device production having an appropriate viscosity does not easily undergo liquid dripping, and can form a wiring pattern with high accuracy by a printing method. Furthermore, the ink can be fired at a lower temperature, and softening and deformation of the coated surface member due to exposure to high temperatures for a long period of time during firing can be prevented. Furthermore, the amount of ash remaining after firing can be significantly reduced, and a decrease in electrical properties caused by the ash can be suppressed.

Therefore, when the solvent composition for electronic device production according to the present invention is used, wiring and the like having excellent electrical properties can be formed by a printing method, and an electronic device including wiring and the like excelling in electrical properties can be efficiently produced.

DESCRIPTION OF EMBODIMENTS

Solvent Composition for Electronic Device Production

The solvent composition for electronic device production (hereinafter, may be referred to as merely a "solvent composition") of an embodiment of the present invention is used in an ink for producing an electronic device using a printing method, and contains a miscible product of: a solvent and a compound represented by Formula (1).

The solvent composition according to an embodiment of the present invention may contain another component in addition to the miscible product of the solvent and compound (1) as long as the another component does not impair the effect, but the ratio of the miscible product to the total amount of the solvent composition of an embodiment of the present invention is, for example, 50 wt. % or greater, preferably 60 wt. % or greater, more preferably 70 wt. % or greater, even more preferably 80 wt. % or greater, particularly preferably 90 wt. % or greater, and most preferably 95 wt. % or greater. Note that the upper limit is 100 wt. %. That is, the solvent composition according to an embodiment of the present invention may contain only the solvent and the compound (1).

The miscible product includes the solvent and the compound (1) as constituent components thereof. The compound (1) excels particularly in an effect of thickening the solvent, and therefore a very small amount of the compound (1) used can impart an appropriate viscosity to the solvent. Thus, the content of the compound (1) with respect to the total amount of the miscible product can be suppressed to a very low amount, and the amount of ash, after firing, originating from the compound (1) can be greatly reduced.

The weight ratio of the solvent (total amount if two or more types are contained) and the compound (1) (total amount if two or more types are contained) constituting the miscible product (the solvent:the compound (1)) is, for example, from 100:0.01 to 100:50, preferably from 100:0.05 to 100:20, particularly preferably from 100:0.1 to 100:10, most preferably from 100:0.5 to 100:5, and above all, preferably from 100:0.5 to 100:3.

The content of the compound (1) in the total amount of the miscible product (100 wt. %) is for example from 0.01 to 50 wt. %, preferably from 0.05 to 20 wt. %, particularly preferably from 0.1 to 10 wt. %, most preferably from 0.5 to 5 wt. %, and above all, preferably from 0.5 to 3 wt. %.

When the content of the compound (1) falls below the range described above, it becomes difficult to stably maintain the viscosity of the miscible product, for example, viscosity reduces due to changes in temperature, and it may be difficult for an ink containing the miscible product to form a wiring pattern with high accuracy due to liquid dripping or the like. On the other hand, when the content of the compound (1) exceeds the range described above, the viscosity of the miscible product becomes too high, and it may be difficult to use ink containing the miscible product in the formation of wiring or the like by a printing method.

The content of the solvent (total amount if two or more types are contained) in the total amount of the miscible product (100 wt. %) is, for example, from 50 to 99.99 wt. %, preferably from 90 to 99.95 wt. %, particularly preferably from 95 to 99.90 wt. %, and most preferably from 97 to 99.5 wt. %.

When the content of the solvent falls below the range described above, the viscosity of the miscible product becomes too high, and it may be difficult to use ink containing the miscible product in the formation of wiring or the like by a printing method. On the other hand, when the content of the solvent exceeds the range described above, it becomes difficult to stably maintain the viscosity of the miscible product, for example, viscosity reduces due to changes in temperature, and it may be difficult for an ink containing the product to form a wiring pattern with high accuracy due to liquid dripping or the like.

The miscible product and the solvent composition according to an embodiment of the present invention containing the same have appropriate viscosities, and the viscosity at 25° C. [at a shear rate of 0.5 s$^{-1}$] is, for example, approximately from 0.01 to 1000 Pa·s, preferably from 0.1 to 500 Pa·s, particularly preferably from 1 to 200 Pa·s, and most preferably from 30 to 150 Pa·s.

Compound (1)

The compound (1) according to an embodiment of the present invention is a compound having an effect of thickening the solvent described below, and is represented by Formula (1) below. One type of the compound (1) may be used alone, or two or more types thereof can be used in combination.

[Chem. 4]

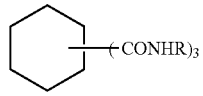

(1)

In the above Formula (1), R is the same or different and represents an aliphatic hydrocarbon group having 1 or more carbon atoms, and examples thereof include: a linear or branched chain alkyl group having approximately from 1 to 30 (preferably from 6 to 25, and particularly preferably from 6 to 15) carbon atoms such as methyl, ethyl, propyl, isopropyl, butyl, t-butyl, pentyl, hexyl, octyl, 2-ethylhexyl, 3,7-dimethyloctyl, decyl, dodecyl, myristyl, stearyl, and nonadecyl groups; a linear or branched chain alkenyl group having approximately from 2 to 30 (preferably from 6 to 25, particularly preferably from 10 to 20, and most preferably from 15 to 20) carbon atoms, such as vinyl, 3-butenyl, 4-pentenyl, 2-hexenyl, 3-hexenyl, 4-hexenyl, 5-hexenyl, 7-octenyl, 9-decenyl, 11-dodecenyl, and oleyl groups; and a linear or branched chain alkynyl group having approximately from 2 to 30 (preferably from 6 to 25, and particularly preferably from 12 to 20) carbon atoms, such as butynyl, pentynyl, hexynyl, octynyl, decynyl, pentadecynyl, and octadecynyl groups.

Examples of the compound (1) include compounds represented by Formula (1-1) or (1-2) below. In the following formulas, R is the same as described above. Of these, in an embodiment of the present invention, the compound represented by Formula (1-1) below is preferable from the perspective of particularly excelling in the effect of thickening the solvent described below.

[Chem. 5]

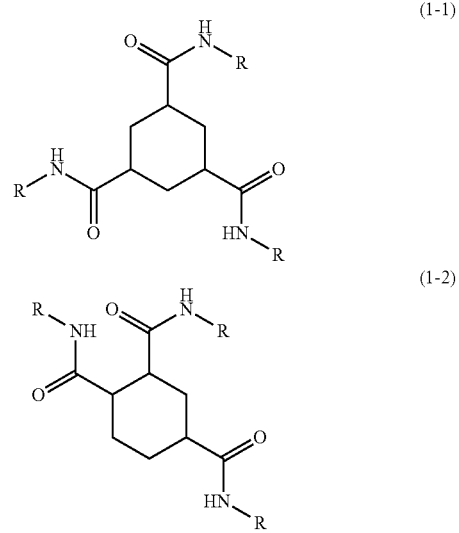

The compound (1) is preferably one having an evaporation temperature from 120 to 380° C. (preferably from 150 to 330° C., more preferably from 150 to 320° C., particularly preferably from 150 to 315° C., and most preferably from 170 to 315° C.), and the evaporation temperature can be controlled by the type of side chains. In a case where the evaporation temperature exceeds the range described above, it becomes difficult to fire the compound (1) at low temperatures, and when ink containing such a compound (1) is fired, the coated surface member may soften and deform due to exposure to high temperatures for a long period of time. On the other hand, in a case where the evaporation temperature of the compound (1) falls below the range described above, when the compound (1) is miscible with the solvent, the composition varies due to the vaporization of the compound (1), and this tends to make it difficult to obtain a miscible product having the desired viscosity. In addition, when printing the ink containing the miscible product of the compound (1) and solvent, the viscosity increases excessively due to vaporization of the compound (1), and this tends to make it difficult to print with good accuracy.

The compound (1) can self-associate through hydrogen bonding at the amide bond sites and form a fibrous self-assembled body. Further, the R group has affinity for the solvent. Therefore, when the compound (1) and the solvent are miscible, the fibrous self-assembled body of the compound (1) can form a mesh structure in a solvent, and consequently, lead to a viscosity as that of a polymer compound. Therefore, the viscosity of the solvent increases, and a miscible product having a stable viscosity over time is formed.

The compound (1) can be produced, for example, through a method in which an cyclohexane tricarboxylic acid is reacted with thionyl chloride to yield cyclohexane tricarbonyl trichloride, and then the resulting cyclohexane tricarbonyl trichloride is reacted with an amine (R—NH$_2$: R is the same as described above).

As the cyclohexane tricarboxylic acid, 1,3,5-cyclohexane tricarboxylic acid and 1,2,5-cyclohexane tricarboxylic acid can be suitably used.

Examples of the amine (R—NH$_2$: R is the same as described above) include amines having an aliphatic hydrocarbon group (for example, a linear or branched chain alkyl group, alkenyl group, or alkynyl group) having 1 or more carbon atoms (preferably from 1 to 30 carbon atoms, and particularly preferably from 6 to 25 carbon atoms), such as butylamine, pentylamine, isopentylamine, hexylamine, octylamine, 2-ethylhexylamine, 3,7-dimethyloctylamine, decylamine, laurylamine, myristylamine, stearylamine, and oleylamine.

The reaction between the cyclohexane tricarbonyl trichloride and the amine can be performed, for example, by adding dropwise the cyclohexane tricarbonyl trichloride into a system charged with the amine. One type of the amine may be used alone, or two or more types may be used in combination.

The usage amount of the amine (total amount when two or more types of amines are used) is, for example, approximately from 4 to 8 moles and preferably from 4 to 6 moles, per mole of the cyclohexane tricarbonyl trichloride.

The reaction between the cyclohexane tricarbonyl trichloride and the amine can be performed in the presence or absence of a solvent. Examples of the solvent include saturated or unsaturated hydrocarbon-based solvents such as pentane, hexane, heptane, octane, and petroleum ether; aromatic hydrocarbon-based solvents such as benzene, toluene, and xylene; halogenated hydrocarbon-based solvents such as methylene chloride, chloroform, 1,2-dichloroethane, chlorobenzene, and bromobenzene; ether-based solvents such as diethyl ether, diisopropyl ether, dibutyl ether, tetrahydrofuran (THF), dioxane, 1,2-dimethoxyethane, and cyclopentyl methyl ether; nitrile-based solvents such as acetonitrile and benzonitrile; sulfoxide-based solvents such as dimethyl sulfoxide; sulfolane-based solvents such as sulfolane; amide-based solvents such as dimethylformamide; and high boiling point solvents such as silicone oils. One type of these solvents may be used alone, or two or more types may be used in combination.

The usage amount of the solvent is, for example, approximately from 50 to 300 wt. % relative to the total amount of the cyclohexane tricarbonyl trichloride and amine. The solvent, when used in an amount greater than the above range, decreases concentrations of the reaction components, and tends to decrease the reaction rate.

The reaction between the cyclohexane tricarbonyl trichloride and amine is typically performed under normal pressure. In addition, the atmosphere of the above reaction is not particularly limited as long as it does not inhibit the reaction. For example, any of an air atmosphere, a nitrogen atmosphere, and an argon atmosphere may be used. The reaction temperature is, for example, approximately from 30 to 60° C. The reaction time is, for example, approximately from 0.5 to 20 hours. After completion of the reaction (=after completion of dropwise addition), aging may be performed. In a case where aging is performed, the aging temperature is, for example, approximately from 30 to 60° C., and the aging time is, for example, approximately from 1 to 5 hours. In addition, the reaction can be performed by any method, such as a batch manner, a semi-batch manner, and a continuous manner.

After the completion of the reaction, the resulting reaction product can be separated and purified by a separation means such as filtration, concentration, distillation, extraction, crystallization, adsorption, recrystallization, and column chromatography, or by a combined separation means thereof.

Solvent

The solvent is a constituent component of the miscible product contained in the solvent composition of an embodiment of the present invention. In an embodiment of the present invention, a solvent excelling in solubility of the compound (1) described above is preferably used.

Among these solvents, the use of one or more types of solvents having an SP value [$(cal/cm^3)^{0.5}$: Fedors' calculated value] at 25° C. in a range from 7.0 to 9.0 (preferably from 7.5 to 9.0 and particularly preferably from 7.8 to 8.5) is preferable in that such solvent excels in solubility of the compound (1), the heating temperature when dissolving the compound (1) can be reduced, and for example, the heating temperature can be suppressed to approximately from 50 to 90° C. A solvent having an SP value outside the range described above exhibits low solubility of the compound (1), and therefore there is a tendency to require heating at a higher temperature when dissolving the compound (1).

Preferably, the solvent used is at least one selected from n-decane (SP value: 7.6), n-dodecane (SP value: 7.7), propylene glycol methyl-n-propyl ether (SP value: 8.1), propylene glycol methyl-n-butyl ether (SP value: 8.1), dipropylene glycol dimethyl ether (SP value: 8.4), dipropylene glycol methyl-n-propyl ether (SP value: 8.2), dipropylene glycol methyl-n-butyl ether (SP value: 8.2), dipropylene glycol methyl isoamyl ether (SP value: 8.0), tripropylene glycol methyl-n-propyl ether (SP value: 8.2), cyclohexyl acetate (SP value: 8.9), 2-methylcyclohexyl acetate (SP value: 8.5), 4-t-butylcyclohexyl acetate (SP value: 8.2), and dihydroterpinyl acetate (SP value: 8.3).

Method for Producing Solvent Composition for Electronic Device Production

The solvent composition for electronic device production of an embodiment of the present invention can be produced, for example, through blending the solvent and the compound (1) to make a miscible material.

The solvent and the compound (1) can be miscible by mixing, heating and dissolving [for example, heating and dissolving at a temperature from 30 to 120° C. (the upper limit is preferably 110° C., and particularly preferably 100° C., and the lower limit is preferably 40° C., particularly preferably 50° C., and most preferably 70° C.)].

The time required for the heating and dissolving is, for example, approximately from 3 to 60 minutes (preferably from 10 to 30 minutes).

After the heating and dissolving, cooling to room temperature (for example, from 1 to 30° C.) or lower is preferably performed. The cooling may be performed by a gradual cooling at room temperature or by rapid cooling using, ice cooling.

By mixing, heating, and dissolving the solvent and the compound (1) as described above, the compound (1) forms a fibrous self-assembled body in the solvent, and further, the self-assembled body forms a mesh structure. As a result, the solvent is thickened, and a miscible product of an embodiment of the present invention is obtained. Therefore, the miscible product of an embodiment of the present invention is a substance in which the solvent is thickened by the self-assembled body of the compound (1).

The solvent composition for electronic device production according to an embodiment of the present invention can be produced by blending, as necessary, another component into the miscible product obtained by the method described above.

Ink for Electronic Device Production

The ink for electronic device production of an embodiment of the present invention (hereinafter, also referred to as "ink") is an ink for forming an electronic device (in particular, wiring and electrodes of an electronic device) by application using a printing method. The ink of an embodiment of the present invention contains the miscible product of the solvent and compound (1) described above.

The content of the miscible product is, for example, 1 wt. % or greater, preferably 10 wt. % or greater, more preferably 30 wt. % or greater, even more preferably 50 wt. % or greater, particularly preferably 70 wt. % or greater, most preferably 80 wt. % or greater, and above all, preferably 90 wt. % or greater of the total amount of the ink (100 wt. %). Note that the upper limit is 100 wt. %. That is, the ink of the present invention may consist of only the miscible product described above.

The ink according to an embodiment of the present invention may contain another component as necessary, in addition to the miscible product described above. Of the another component, the ink of an embodiment of the present invention preferably contains at least one type of electrical property imparting material selected from conductive metal materials, semiconductor materials, magnetic materials, dielectric materials, or insulating materials.

As the conductive metal materials and magnetic materials, known and commonly used materials can be used, and examples thereof include gold, silver, copper, nickel, palladium, aluminum, iron, platinum, molybdenum, tungsten, zinc, lead, cobalt, iron oxide and chromium oxide, ferrite, and alloys thereof. Known and commonly used semiconductor materials can be used as the semiconductor materials, and examples thereof include pentacene, fullerene derivatives, polythiophene derivatives, metals (copper, indium, gallium, selenium, arsenic, cadmium, tellurium, and alloys thereof), and silicon fine particles. Known and common used materials can be used as the dielectric material and insulating material, and examples thereof include cycloolefin polymers, fluororesins, butyral resins, glass, paper, and Teflon (trade name).

The content of the electrical property imparting material (total amount when two or more types are contained) is, for example, approximately from 0.1 to 30 wt. %, preferably from 0.1 to 20 wt. %, particularly preferably from 0.1 to 10 wt. %, most preferably from 0.1 to 5 wt. %, and above all, preferably from 0.1 to 3 wt. % of the total amount of the ink (100 wt. %).

The proportion of the total content of the miscible product and the electrical property imparting material in the total amount of the ink of an embodiment of the present invention is, for example, 60 wt. % or greater, preferably 70 wt. % or greater, particularly preferably 80 wt. % or greater, most preferably 90 wt. % or greater, and above all, preferably 95 wt. % or greater. Note that the upper limit is 100 wt. %.

Since the ink of an embodiment of the present invention contains the miscible product described above having an appropriate viscosity, the ink has a viscosity that is suited for forming an electronic device with high precision by a printing method even without blending a binder resin.

The ink of an embodiment of the present invention has an appropriate viscosity, and the viscosity at 25° C. [at a shear rate of 0.5 s$^{-1}$] is, for example, approximately from 0.01 to 1000 Pa·s, preferably from 0.1 to 500 Pa·s, particularly preferably from 1 to 200 Pa·s, and most preferably from 30 to 150 Pa·s.

Therefore, the ink of an embodiment of the present invention does not require the addition of a binder resin (for example, a polymer compound having a molecular weight of 10000 or greater, such as ethyl cellulose resin, alkyl cellulose resin, polyvinyl acetal resin, and acrylic resin), and even in a case where a binder resin is added, the addition amount is, with respect to the total amount of the ink (100 wt. %), for example, 10 wt. % or less, preferably 5 wt. % or less, particularly preferably 3 wt. % or less, and most preferably 1 wt. % or less. In a case where the addition amount of the binder resin exceeds the range described above, a reduction in electrical properties is caused by the ash originating from the binder resin and generated by firing, and thus such an addition amount is not preferable.

Furthermore, the miscible product described above contained in the ink of an embodiment of the present invention excels in thermal decomposability and its molecular weight is easily reduced. Therefore, the ink of an embodiment of the present invention can be fired at a lower temperature (for example, from 100 to 350° C., preferably from 150 to 300° C., and particularly preferably from 150 to 250° C.) compared to ink having viscosity imparted by a binder resin such as ethyl cellulose, and softening and deformation of the coated surface member in the firing can be prevented. Furthermore, the amount of ash remaining after firing can be significantly reduced, and a decrease in electrical properties caused by the ash can be suppressed.

According to the ink of an embodiment of the present invention, wiring and the like excelling in electrical properties (for example, electric conductivity or insulating properties) can be formed with high precision through applying the ink through a printing method onto a surface member to be coated (for example, a ceramic substrate, a green sheet, and the like), and then drying and firing the coated surface member. Therefore, the ink of an embodiment of the present invention is particularly useful as an ink for producing wiring and electrodes of a capacitor, inductor, varistor, thermistor, speaker, actuator, antenna, or solid oxide fuel cell (SOFC) (particularly, a laminated ceramic capacitor).

EXAMPLES

Hereinafter, the present invention is described in greater detail based on examples, but the present invention is not limited in any way by these examples.

Preparation Example 1 [Synthesis of Thickener (1): 1,3,5-cyclohexane tricarbonyl 1,3,5-tri(3,7-dimethyloctylamide)]

5.0 g (0.023 mol) of 1,3,5-cyclohexane tricarboxylic acid was charged to a 100 mL 4-neck separable flask equipped with a Dimroth condenser, a nitrogen inlet, a dripping funnel, and a thermocouple, after which an excess amount of 50 mL of thionyl chloride was added thereto, and the mixture was refluxed overnight. As a result, a clear solution was obtained. Subsequently, hexane was added to the clear solution, concentration under reduced pressure was repeated three times, and 5.9 g (0.022 mol) of 1,3,5-cyclohexane tricarbonyl 1,3,5-trichloride as a white solid was thereby obtained. Note that the white solid was confirmed by FT-IR to be an acid chloride rather than an acid anhydride.

Next, 11.5 g (0.073 mol) of 3,7-dimethyloctylamine was charged to a 500 mL Schlenk round bottom flask and dissolved with 150 mL of dehydrated THF, and then 25 mL of dehydrated triethylamine was added, and the mixture was cooled with ice. An entire amount of 50 mL of a dehydrated THF solution with 5.9 g of 1,3,5-cyclohexane tricarbonyl 1,3,5-trichloride obtained as described above was added dropwise to this mixed solution under cooling with ice, and the mixture was stirred for 1 hour at 0° C. Next, the mixture was stirred at room temperature overnight, and then stirred at 60° C. for 2 hours.

The insoluble matter was filtered off, washed with THF and acetone, and dried under reduced pressure using an evaporator, after which the solid was suspended in hot ethanol, and water was further added. The insoluble matter was filtered off, washed again with acetone, and then dried under reduced pressure using an evaporator. The obtained solid was dissolved in hot DMSO and returned to room temperature to precipitate crystals, and after the precipitated crystals were washed with acetone and dried under reduced pressure, 11.4 g (0.018 mol, yield of 78%) of a white solid was obtained. The white solid was identified as being 1,3,5-cyclohexane tricarbonyl 1,3,5-tri(3,7-dimethyloctylamide) through elemental analysis and $^1$H-NMR.

Preparation Example 2 [Synthesis of Thickener (2): 1,3,5-cyclohexane tricarbonyl 1,3,5-trioleylamide]

17.4 g (0.018 mol, yield of 77%) of 1,3,5-cyclohexane tricarbonyl 1,3,5-trioleylamide was obtained in the same manner as in Preparation Example 1 with the exception that 19.5 g (0.073 mol) of oleylamine was used in place of the 3,7-dimethyloctylamine.

Example 1

The thickener (1) obtained in Preparation Example 1 was added to dihydroterpinyl acetate (DHTA) as a solvent so that the thickener concentration was 1 wt. %, and this mixture was heated and dissolved for 0.5 hours at a liquid temperature of 100° C., and then cooled to 25° C. to obtain a paste-like miscible product, which was then used as an ink. The viscosity at 25° C. [at a shear rate of 0.5 s$^{-1}$] of the obtained ink was 80 Pa·s.

Examples 2 and 3 and Comparative Examples 1 to 3

Inks were obtained in the same manner as in Example 1 with the exception that the formulations were modified as described in Table 1 (unit: wt. %). Note that in the Comparative Examples, ethyl cellulose (EC200) was used as a thickener, and was added to the solvent so that the concentration was as described in Table 1, and the mixtures were each heated and dissolved for 3 hours at a liquid temperature of 80° C., and cooled at 25° C. to obtain paste-like inks.

Evaluation

The residual ash amount and coatability of the inks obtained in the Examples and Comparative Examples were evaluated according to the following methods.

Residual Ash Content:

For 20 mg of each of inks, a measurement was carried out during a temperature increase at 10° C./minute from 20° C. to 400° C. using a TG-DTA, and the weight at each temperature was measured. The amount of residual ash (percentage of residual ash based on the total amount of the ink) at 250° C. was evaluated.

Coatability:

A screen printer (trade name "TV screen printer, model LS-150 type", available from Newlong Seimitsu Kogyo Co., Ltd.) was used, and inks for which coating was achieved were evaluated as being "good", and inks for which coating was not achieved were evaluated as being "poor".

The results are summarized in the table below.

TABLE 1

| | Composition (wt. %) | | | | | Residual Ash Amount (wt. %) | Coatability |
|---|---|---|---|---|---|---|---|
| | Thickener | | | Solvent | | | |
| | 1 | 2 | EC200 | DPMIA | DHTA | | |
| Example 1 | 1 | | | | 99 | 0.8 | Good |
| Example 2 | | 1 | | | 99 | 0.8 | Good |
| Example 3 | | 1 | | 99 | | 0.8 | Good |
| Comparative Example 1 | | | 1 | | 99 | 0.9 | Poor |
| Comparative Example 2 | | | 3 | | 97 | 2.8 | Poor |
| Comparative Example 3 | | | 5 | | 95 | 4.7 | Good |

The abbreviations in Table 1 are as follows.

Thickener
  1: 1,3,5-cyclohexane tricarbonyl 1,3,5-tri(3,7-dimethyloctylamide) obtained in Preparation Example 1 was used.
  2: 1,3,5-cyclohexane tricarbonyl 1,3,5-trioleylamide obtained in Preparation Example 2 was used.
  EC200: Ethyl cellulose, trade name: "Ethocel STD200", available from Nisshin Kasei Co., Ltd.

Solvent
  DPMIA: Dipropylene glycol methyl isoamyl ether, available from Daicel Corporation, SP value: 8.0
  DHTA: Dihydroterpinyl acetate, available from Nippon Koryo Yakuhin Kaisha, Ltd., SP value: 8.3

From Table 1, the inks of the Examples in which a compound represented by Formula (1) was used as a thickener had an appropriate viscosity even when the usage amount of the thickener was extremely small, and exhibited excellent coatability. Furthermore, even when the inks of the Examples were fired at a low temperature, the residual ash amount after firing was suppressed to a very low level. In contrast, ethyl cellulose was used as a thickener in the inks of the Comparative Examples, and thus an appropriate viscosity was not obtained unless a larger amount of the thickener was added in comparison to the inks of the Examples. As a result of adding a large amount of the thickener, a large amount of ash remained after firing at low temperatures. From the above, it was found that good coatability and a suppression of residual ash could not be simultaneously achieved with the typical inks, while in contrast, the inks of an embodiment of the present invention can simultaneously achieve good coatability and a suppression of residual ash amount.

In summary, configurations of the present invention and variations thereof are described below.

[1] A solvent composition for electronic device production, which is used in an ink for producing an electronic device by a printing method, the solvent composition containing a miscible product of: a solvent and a compound represented by Formula (1) below:

[Chem. 6]

$$\text{cyclohexane}{-}(\text{CONHR})_3 \tag{1}$$

wherein R is the same or different and represents an aliphatic hydrocarbon group having 1 or more carbon atoms.

[2] The solvent composition for electronic device production according to [1], wherein in Formula (1), R is the same or different and represents: a linear or branched chain alkyl group having from 1 to 30 carbon atoms including methyl, ethyl, propyl, isopropyl, butyl, t-butyl, pentyl, hexyl, octyl, 2-ethylhexyl, 3,7-dimethyl octyl, decyl, dodecyl, myristyl, stearyl, and nonadecyl groups; a linear or branched chain alkenyl group having approximately from 2 to 30 carbon atoms including vinyl, 3-butenyl, 4-pentenyl, 2-hexenyl, 3-hexenyl, 4-hexenyl, 5-hexenyl, 7-octenyl, 9-decenyl, 11-dodecenyl, and oleyl groups; and a linear or branched chain alkynyl group having from 2 to 30 carbon atoms including butynyl, pentynyl, hexynyl, octynyl, decynyl, pentadecynyl, and octadecynyl groups.

[3] The solvent composition for electronic device production according to [1] or [2], wherein R in Formula (1) is a linear or branched chain alkyl group, alkenyl group, or alkynyl group having from 6 to 25 carbon atoms.

[4] The solvent composition for electronic device production according to any one of [1] to [3], wherein the compound represented by Formula (1) is represented by the Formula (1-1) or (1-2) below:

[Chem. 7]

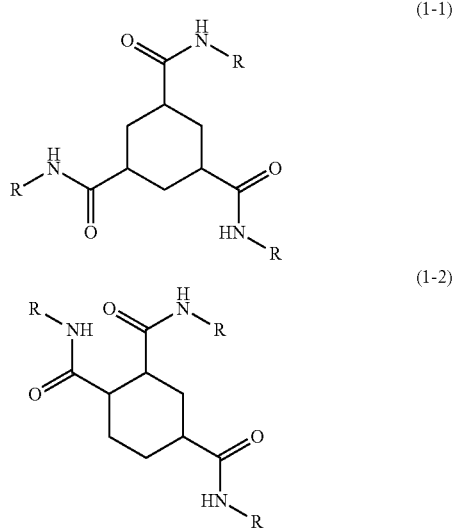

(1-1)

(1-2)

[5] The solvent composition for electronic device production according to any one of [1] to [4], wherein the compound represented by Formula (1) is 1,3,5-cyclohexane tricarbonyl 1,3,5-tri(3,7-dimethyloctylamide) or 1,3,5-cyclohexane tricarbonyl 1,3,5-trioleylamide.

[6] The solvent composition for electronic device production according to any one of [1] to [5], wherein an SP value $[(cal/cm^3)^{0.5}]$ of the solvent at 25° C. is from 7.0 to 9.0.

[7] The solvent composition for electronic device production according to any one of [1] to [6], wherein the solvent is at least one selected from n-decane, n-dodecane, propylene glycol methyl-n-propyl ether, propylene glycol methyl-n-butyl ether, dipropylene glycol dimethyl ether, dipropylene glycol methyl-n-propyl ether, dipropylene glycol methyl-n-butyl ether, dipropylene glycol methyl isoamyl ether, tripropylene glycol methyl-n-propyl ether, cyclohexyl acetate, 2-methylcyclohexyl acetate, 4-t-butylcyclohexyl acetate, and dihydroterpinyl acetate.

[8] The solvent composition for electronic device production according to any one of [1] to [7], wherein a weight ratio of the solvent to the compound represented by Formula (1) constituting the miscible product (the solvent:the compound) is from 100:0.01 to 100:50.

[9] The solvent composition for electronic device production according to [8], wherein the weight ratio of the solvent (total amount if two or more types are contained) to the compound (1) (total amount if two or more types are contained) constituting the miscible product (the solvent: the compound) is from 100:0.01 to 100:50, from 100:0.05 to 100:20, from 100:0.1 to 100:10, from 100:0.5 to 100:5, or from 100:0.5 to 100:3.

[10] A method for producing a solvent composition for electronic device production, wherein the solvent composition for electronic device production according to any one of [1] to [9] is obtained through blending a solvent and a compound to make a miscible material, the compound being represented by the Formula (1) below:

[Chem. 8]

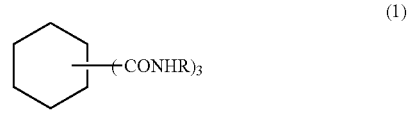

(1)

wherein R is the same or different and represents an aliphatic hydrocarbon group having 1 or more carbon atoms.

[11] The method for producing a solvent composition for electronic device production according to [10], wherein the temperature for heating and melting in the blending is from 30 to 120° C., an upper limit of the temperature is 110° C. or 100° C., and a lower limit of the temperature is 40° C., 50° C., or 70° C.

[12] An ink for electronic device production, the ink containing a miscible product of: a solvent and a compound represented by the Formula (1) below:

[Chem. 9]

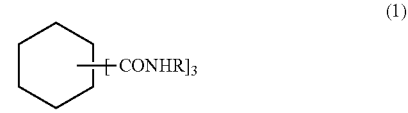

(1)

wherein R is the same or different and represents an aliphatic hydrocarbon group having 1 or more carbon atoms.

[13] The ink for electronic device production according to [12], wherein a content of the miscible product is, per 100 wt. % of the total amount of the ink, 1 wt. % or greater, 10 wt. % or greater, 30 wt. % or greater, 50 wt. % or greater, 70 wt. % or greater, 80 wt. % or greater, or 90 wt. % or greater, and an upper limit is 100 wt. %.

[14] The ink for electronic device production according to [12] or [13], further containing an electrical property imparting material.

[15] The ink for electronic device production according to [14], wherein the electrical property imparting material is at least one type of electrical property imparting material selected from conductive metal materials, semiconductor materials, magnetic materials, dielectric materials, or insulating materials.

[16] The ink for electronic device production according to any one of [12] to [15], wherein a binder resin content is 10 wt. % or less.

[17] The ink for electronic device production according to [16], wherein the binder resin content is, per 100 wt. % of the total amount of the ink, 10 wt. % or less, 5 wt. % or less, 3 wt. % or less, or 1 wt. % or less.

[18] Use of a solvent composition in an ink for producing an electronic device by a printing method, the solvent composition containing a miscible product of: a solvent and a compound represented by the Formula (1) below:

[Chem. 10]

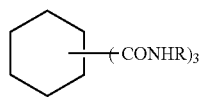
(1)

wherein R is the same or different and represents an aliphatic hydrocarbon group having 1 or more carbon atoms.

[19] The use of a solvent composition according to [18], wherein in Formula (1), R is the same or different and represents: a linear or branched chain alkyl group having from 1 to 30 carbon atoms including methyl, ethyl, propyl, isopropyl, butyl, t-butyl, pentyl, hexyl, octyl, 2-ethylhexyl, 3,7-dimethyl octyl, decyl, dodecyl, myristyl, stearyl, and nonadecyl groups; a linear or branched chain alkenyl group having approximately from 2 to 30 carbon atoms including vinyl, 3-butenyl, 4-pentenyl, 2-hexenyl, 3-hexenyl, 4-hexenyl, 5-hexenyl, 7-octenyl, 9-decenyl, 11-dodecenyl, and oleyl groups; and a linear or branched chain alkynyl group having from 2 to 30 carbon atoms including butynyl, pentynyl, hexynyl, octynyl, decynyl, pentadecynyl, and octadecynyl groups.

[20] The use of a solvent composition according to [18] or [19], wherein R in Formula (1) is a linear or branched chain alkyl group, alkenyl group, or alkynyl group having from 6 to 25 carbon atoms.

[21] The use of a solvent composition according to any one of [18] to [20], wherein the compound represented by Formula (1) is represented by the Formula (1-1) or (1-2) below:

[Chem. 11].

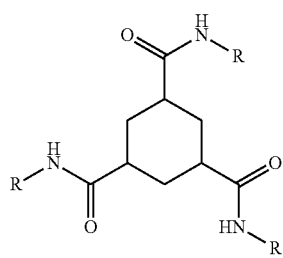
(1-1)

-continued

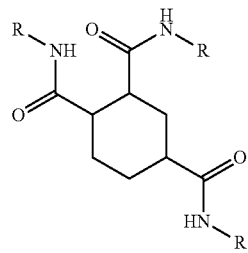
(1-2)

[22] The use of a solvent composition according to any one of [18] to [21], wherein the compound represented by Formula (1) is 1,3,5-cyclohexane tricarbonyl 1,3,5-tri(3,7-dimethyloctylamide) or 1,3,5-cyclohexane tricarbonyl 1,3,5-trioleylamide.

[23] The use of a solvent composition according to any one of [18] to [22], wherein an SP value [$(cal/cm^3)^{0.5}$] of the solvent at 25° C. is from 7.0 to 9.0.

[24] The use of a solvent composition according to any one of [18] to [23], wherein the solvent is at least one selected from n-decane, n-dodecane, propylene glycol methyl-n-propyl ether, propylene glycol methyl-n-butyl ether, dipropylene glycol dimethyl ether, dipropylene glycol methyl-n-propyl ether, dipropylene glycol methyl-n-butyl ether, dipropylene glycol methyl isoamyl ether, tripropylene glycol methyl-n-propyl ether, cyclohexyl acetate, 2-methylcyclohexyl acetate, 4-t-butylcyclohexyl acetate, and dihydroterpinyl acetate.

[25] The use of a solvent composition according to any one of [18] to [24], wherein a weight ratio of the solvent to the compound represented by Formula (1) constituting the miscible product (the solvent:the compound) is from 100:0.01 to 100:50.

[26] The use of a solvent composition according to [25], wherein the weight ratio of the solvent (total amount if two or more types are contained) to the compound (1) (total amount if two or more types are contained) constituting the miscible product (the solvent:the compound) is from 100:0.01 to 100:50, from 100:0.05 to 100:20, from 100:0.1 to 100:10, from 100:0.5 to 100:5, or from 100:0.5 to 100:3.

[27] Use of an ink for producing an electronic device, the ink containing a miscible product of: a solvent and a compound represented by the Formula (1) below:

[Chem. 12]

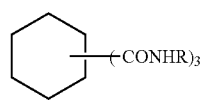
(1)

wherein R is the same or different and represents an aliphatic hydrocarbon group having 1 or more carbon atoms.

[28] The use of an ink for producing an electronic device according to [27], wherein in the ink, a content of the miscible product is, per 100 wt. % of the total amount of the ink, 1 wt. % or greater, 10 wt. % or greater, 30 wt. % or greater, 50 wt. % or greater, 70 wt. % or greater, 80 wt. % or greater, or 90 wt. % or greater, and an upper limit is 100 wt. %.

[29] The use of an ink for electronic device production according to [27] or [28], the ink further containing an electrical property imparting material.

[30] The use of an ink for electronic device production according to [29], wherein the electrical property imparting material is at least one type of electrical property imparting material selected from conductive metal materials, semiconductor materials, magnetic materials, dielectric materials, or insulating materials.

[31] The use of an ink for electronic device production according to any one of [27] to [30], wherein a binder resin content is 10 wt. % or less.

[32] The use of an ink for electronic device production according to [31], wherein the binder resin content is, per 100 wt. % of the total amount of the ink, 10 wt. % or less, 5 wt. % or less, 3 wt. % or less, or 1 wt. % or less.

[33] A solvent composition containing a miscible product of: a solvent and a compound represented by the Formula (1) below:

[Chem. 13]

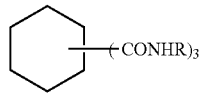
(1)

wherein R is the same or different and represents an aliphatic hydrocarbon group having 1 or more carbon atoms.

[34] The solvent composition according to [33], wherein in Formula (1), R is the same or different and represents: a linear or branched chain alkyl group having from 1 to 30 carbon atoms including methyl, ethyl, propyl, isopropyl, butyl, t-butyl, pentyl, hexyl, octyl, 2-ethylhexyl, 3,7-dimethyl octyl, decyl, dodecyl, myristyl, stearyl, and nonadecyl groups; a linear or branched chain alkenyl group having approximately from 2 to 30 carbon atoms including vinyl, 3-butenyl, 4-pentenyl, 2-hexenyl, 3-hexenyl, 4-hexenyl, 5-hexenyl, 7-octenyl, 9-decenyl, 11-dodecenyl, and oleyl groups; and a linear or branched chain alkynyl group having from 2 to 30 carbon atoms including butynyl, pentynyl, hexynyl, octynyl, decynyl, pentadecynyl, and octadecynyl groups.

[35] The solvent composition according to [33] or [34], wherein R in Formula (1) is a linear or branched chain alkyl group, alkenyl group, or alkynyl group having from 6 to 25 carbon atoms.

[36] The solvent composition according to any one of [33] to [35], wherein the compound represented by Formula (1) is represented by Formula (1-1) or (1-2) below:

[Chem. 14]

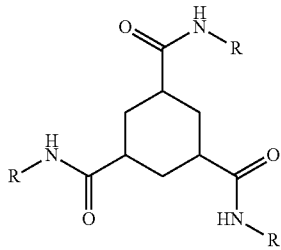
(1-1)

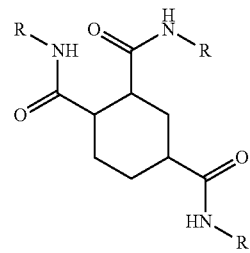
(1-2)

[37] The solvent composition according to any one of [33] to [36], wherein the compound represented by Formula (1) is 1,3,5-cyclohexane tricarbonyl 1,3,5-tri(3,7-dimethyloctylamide) or 1,3,5-cyclohexane tricarbonyl 1,3,5-trioleylamide.

[38] The solvent composition according to any one of [33] to [37], wherein an SP value $[(cal/cm^3)^{0.5}]$ of the solvent at 25° C. is from 7.0 to 9.0.

[39] The solvent composition according to any one of [33] to [38], wherein the solvent is at least one selected from n-decane, n-dodecane, propylene glycol methyl-n-propyl ether, propylene glycol methyl-n-butyl ether, dipropylene glycol dimethyl ether, dipropylene glycol methyl-n-propyl ether, dipropylene glycol methyl-n-butyl ether, dipropylene glycol methyl isoamyl ether, tripropylene glycol methyl-n-propyl ether, cyclohexyl acetate, 2-methylcyclohexyl acetate, 4-t-butylcyclohexyl acetate, and dihydroterpinyl acetate.

[40] The solvent composition according to any one of [33] to [39], wherein a weight ratio of the solvent to the compound represented by Formula (1) constituting the miscible product (the solvent:the compound) is from 100:0.01 to 100:50.

[41] The solvent composition according to [40], wherein the weight ratio of the solvent (total amount if two or more types are contained) to the compound (1) (total amount if two or more types are contained) constituting the miscible product (the solvent:the compound) is from 100:0.01 to 100:50, from 100:0.05 to 100:20, from 100:0.1 to 100:10, from 100:0.5 to 100:5, or from 100:0.5 to 100:3.

[42] An ink containing a miscible product of: a solvent and a compound represented by Formula (1) below:

[Chem. 15]

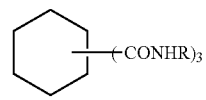
(1)

wherein R is the same or different and represents an aliphatic hydrocarbon group having 1 or more carbon atoms.

[43] The ink according to [42], wherein a content of the miscible product is, per 100 wt. % of the total amount of the ink, 1 wt. % or greater, 10 wt. % or greater, 30 wt. % or greater, 50 wt. % or greater, 70 wt. % or greater, 80 wt. % or greater, or 90 wt. % or greater, and an upper limit is 100 wt. %.

[44] The ink according to [42] or [43], further containing an electrical property imparting material.

[45] The ink according to [44], wherein the electrical property imparting material is at least one type of electrical property imparting material selected from conductive metal materials, semiconductor materials, magnetic materials, dielectric materials, or insulating materials.

[46] The ink according to any one of [42] to [45], wherein a binder resin content is 10 wt. % or less.

[47] The ink according to [46], wherein the binder resin content is, per 100 wt. % of the total amount of the ink, 10 wt. % or less, 5 wt. % or less, 3 wt. % or less, or 1 wt. % or less.

INDUSTRIAL APPLICABILITY

The solvent composition for electronic device production of the present invention has an appropriate viscosity.

In addition, the ink containing the solvent composition for electronic device production having an appropriate viscosity does not easily undergo liquid dripping, and can form a wiring pattern with high accuracy by a printing method. Furthermore, the ink can be fired at a lower temperature, and softening and deformation of the coated surface member due to exposure to high temperatures for a long period of time during firing can be prevented. Furthermore, the amount of ash remaining after firing can be significantly reduced, and a decrease in electrical properties caused by the ash can be suppressed.

Therefore, when the solvent composition for electronic device production according to the present invention is used, wiring and the like having excellent electrical properties can be formed by a printing method, and an electronic device including wiring and the like excelling in electrical properties can be efficiently produced.

The invention claimed is:

1. A method for electronic device production using a solvent composition which is used in an ink for producing an electronic device by a printing method, comprising:
    applying to a surface member by a printing method an ink comprising a miscible product of: a solvent and a compound represented by Formula (1) below:

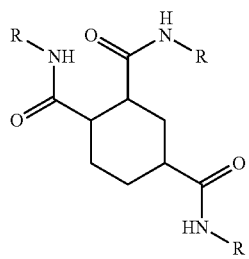

(1)

wherein R is the same or different and represents an aliphatic hydrocarbon group having 1 or more carbon atoms,
wherein the solvent is at least one selected from propylene glycol methyl-n-propyl ether, propylene glycol methyl-n-butyl ether, dipropylene glycol methyl-n-propyl ether, dipropylene glycol methyl-n-butyl ether, dipropylene glycol methyl isoamyl ether, tripropylene glycol methyl-n-propyl ether, cyclohexyl acetate, 2-methylcyclohexyl acetate, 4-t-butylcyclohexyl acetate, and dihydroterpinyl acetate, and
wherein a weight ratio of the solvent to the compound represented by Formula (1) constituting the miscible product, the solvent:the compound, is from 100:0.01 to 100:50.

2. The method for electronic device production according to claim 1, wherein R in Formula (1) is a linear or branched chain alkyl group, alkenyl group, or alkynyl group having from 6 to 25 carbon atoms.

3. The method for electronic device production according to claim 1, wherein an SP value [(cal/cm$^3$)$^{0.5}$] of the solvent at 25° C. is from 7.0 to 9.0.

4. The method for electronic device production according to claim 1, the method further comprising preparing the solvent composition through blending the solvent and the compound represented by Formula (1) to make the miscible product.

5. The method for electronic device production of claim 1, wherein the ink is used to form a wiring pattern by said printing method.

6. The method for electronic device production of claim 1, which comprises a step of firing the ink.

7. The method for electronic device production of claim 1, wherein the surface member is a ceramic substrate or a green sheet.

8. The method for electronic device production of claim 1, wherein the surface member is dried and then fired after the ink is applied thereto.

9. A method for electronic device production, comprising:
    applying to a surface member by a printing method an ink comprising a miscible product of: a solvent and a compound represented by Formula (1) below:

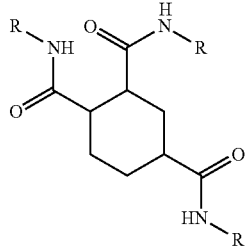

(1)

wherein R is the same or different and represents an aliphatic hydrocarbon group having 1 or more carbon atoms,
wherein the solvent is at least one selected from propylene glycol methyl-n-propyl ether, propylene glycol methyl-n-butyl ether, dipropylene glycol methyl-n-propyl ether, dipropylene glycol methyl-n-butyl ether, dipropylene glycol methyl isoamyl ether, tripropylene glycol methyl-n-propyl ether, cyclohexyl acetate, 2-methylcyclohexyl acetate, 4-t-butylcyclohexyl acetate, and dihydroterpinyl acetate, and
wherein a weight ratio of the solvent to the compound represented by Formula (1) constituting the miscible product, the solvent:the compound, is from 100:0.01 to 100:50.

10. The method for electronic device production according to claim 9, wherein the ink further comprises an electrical property imparting material.

11. The method for electronic device production according to claim 9, wherein a binder resin content of the ink is 10 wt. % or less.

12. The method for electronic device production of claim 10, wherein the electrical property imparting material comprises at least one of from conductive metal materials, semiconductor materials, magnetic materials, dielectric materials, or insulating materials.

13. The method for electronic device production according to claim 9,
   wherein the ink consists of said miscible product and optionally an electrical property imparting material and/or a binder in an amount of not greater than 10 wt. %.

14. The method for electronic device production according to claim 13,
   wherein the ink contains 0.1 to 30 wt. % of said electrical property imparting material.

15. The method for electronic device production according to claim 14,
   wherein the ink consists of said miscible product and optionally an electrical property imparting material and a binder in an amount of not greater than 10 wt. %.

16. The method for electronic device production according to claim 15,
   wherein the ink contains said binder in an amount of 1 wt. % or less.

17. The method for electronic device production according to claim 14,
   wherein the ink does not contain said binder.

18. The method for electronic device production according to claim 13,
   wherein the ink does not contain said binder.

* * * * *